United States Patent [19]

Schmidt et al.

[11] 4,381,390

[45] Apr. 26, 1983

[54] THERMOPLASTIC POLYPHOSPHONATOPHENYL ESTER CARBONATE FROM ARYLOXYCARBONYLOXY-BENZOIC ACID ARYL ESTER AND PREPARATION THEREOF

[75] Inventors: Manfred Schmidt, New Martinsville, W. Va.; Ludwig Bottenbruch, Krefeld, Fed. Rep. of Germany

[73] Assignees: Mobay Chemical Corporation, Pittsburgh, Pa.; Bayer Aktiengesellschaft, Leverkusen, Fed. Rep. of Germany

[21] Appl. No.: 311,360

[22] Filed: Oct. 15, 1981

[51] Int. Cl.$^3$ .............................................. C08G 63/32
[52] U.S. Cl. .................................... 528/167; 528/206
[58] Field of Search ......................................... 528/167

[56] References Cited

U.S. PATENT DOCUMENTS

| | | |
|---|---|---|
| 2,682,522 | 6/1954 | Coover, Jr. et al. ................. 260/47 |
| 2,716,101 | 8/1955 | Coover, Jr. et al. ................. 260/61 |
| 2,891,915 | 6/1959 | McCormack et al. ................. 260/2 |
| 3,719,727 | 3/1973 | Masai et al. ......................... 260/860 |
| 3,919,363 | 11/1975 | Ura et al. ............................. 260/973 |
| 3,946,093 | 3/1976 | Koto et al. ........................... 260/973 |
| 4,046,724 | 9/1977 | Kato et al. ............................ 260/9 |

FOREIGN PATENT DOCUMENTS 21216 1/1981 European Pat. Off. ............ 528/167

OTHER PUBLICATIONS

English Translation of German 3,001,863.
English Translation of German 2,925,208.

*Primary Examiner*—Harold D. Anderson
*Attorney, Agent, or Firm*—Gene Harsh; Lawrence S. Pope; Aron Preis

[57] ABSTRACT

A two step catalyzed process for the preparation of thermoplastic polyphosphonatophenyl ester carbonates comprising first, the preparation of an aryloxy carbonyloxy-benzoic acid aryl ester and second, its transesterification with a phosphonic acid diphenyl ester and a diphenol is disclosed.

7 Claims, 4 Drawing Figures

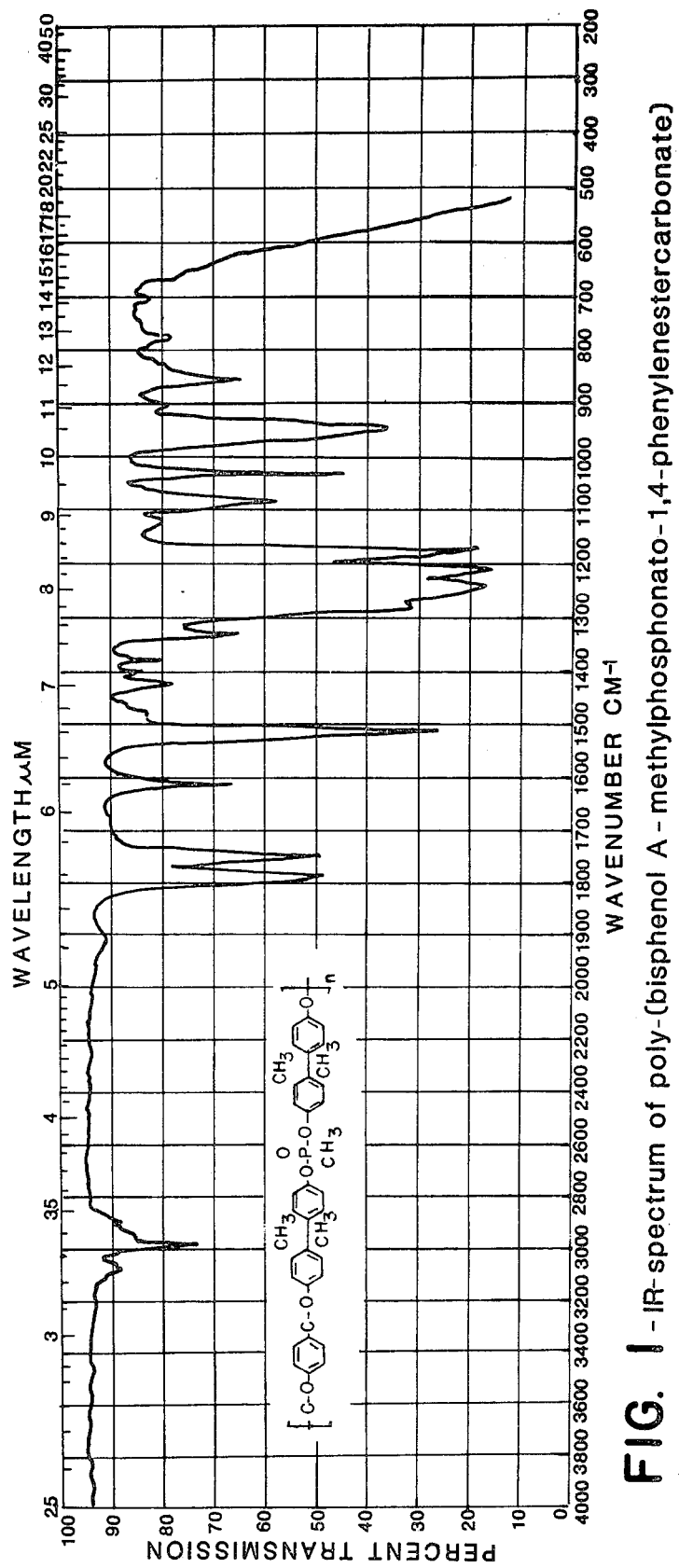
FIG. 1 - IR-spectrum of poly-(bisphenol A-methylphosphonato-1,4-phenylenestercarbonate)

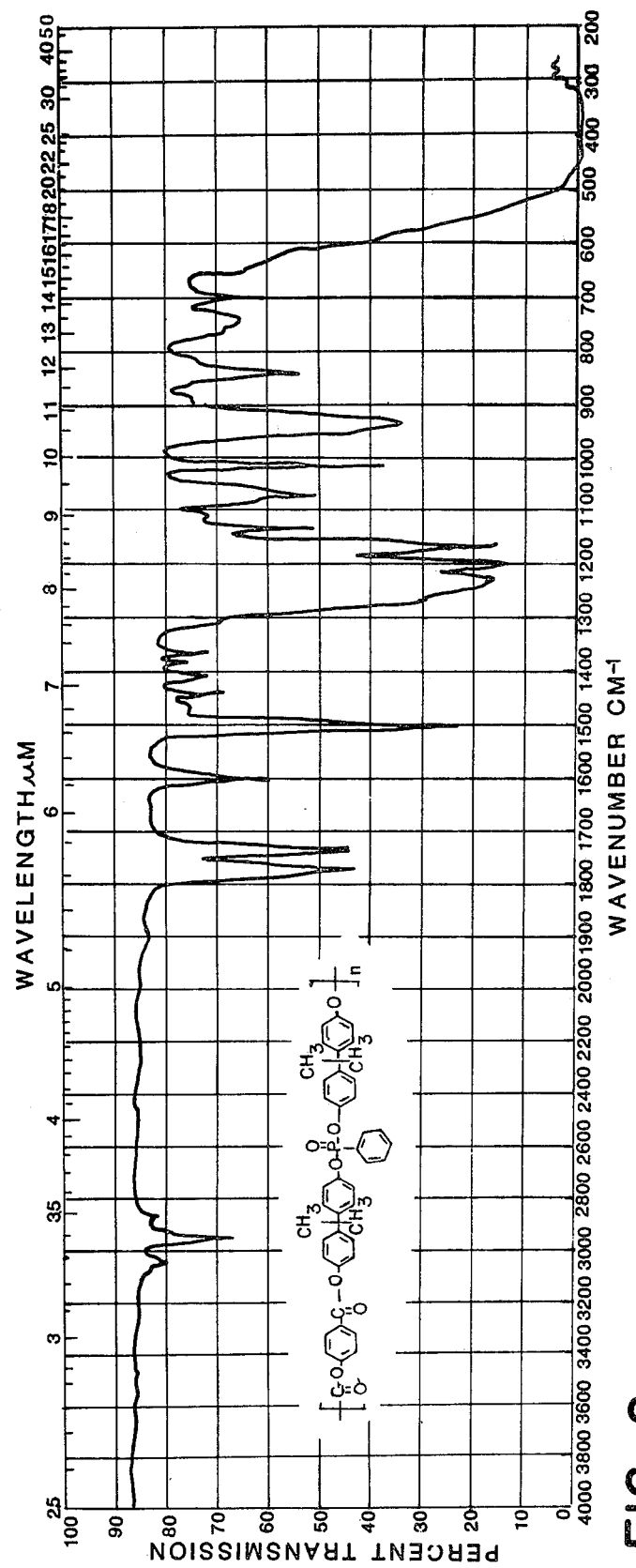
FIG. 2 — IR-spectrum of poly-(bisphenol A-phenylphosphonato-1,4-phenylenestercarbonate)

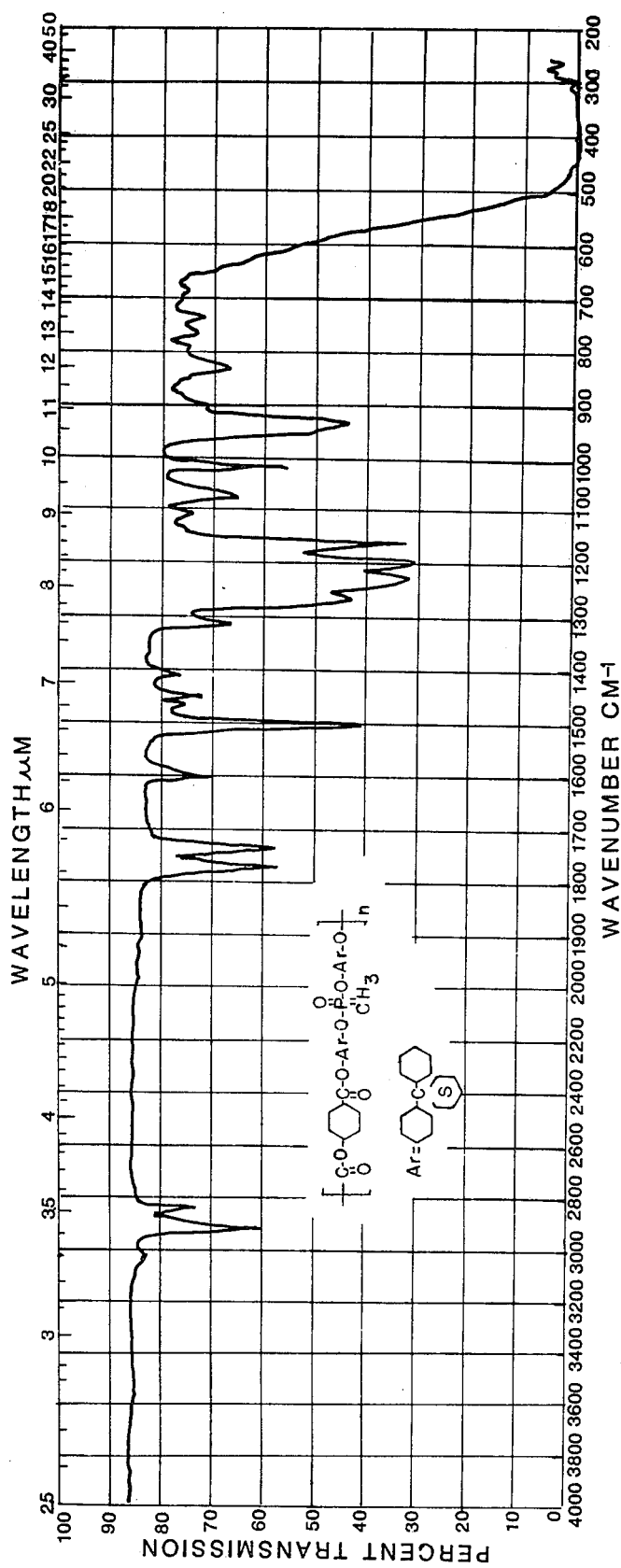
FIG. 3 —IR-spectrum of poly-(1,1-bis-(4-oxyphenyl)cyclohexyliden)-methylphosphonato-1,4-phenylenestercarbonate

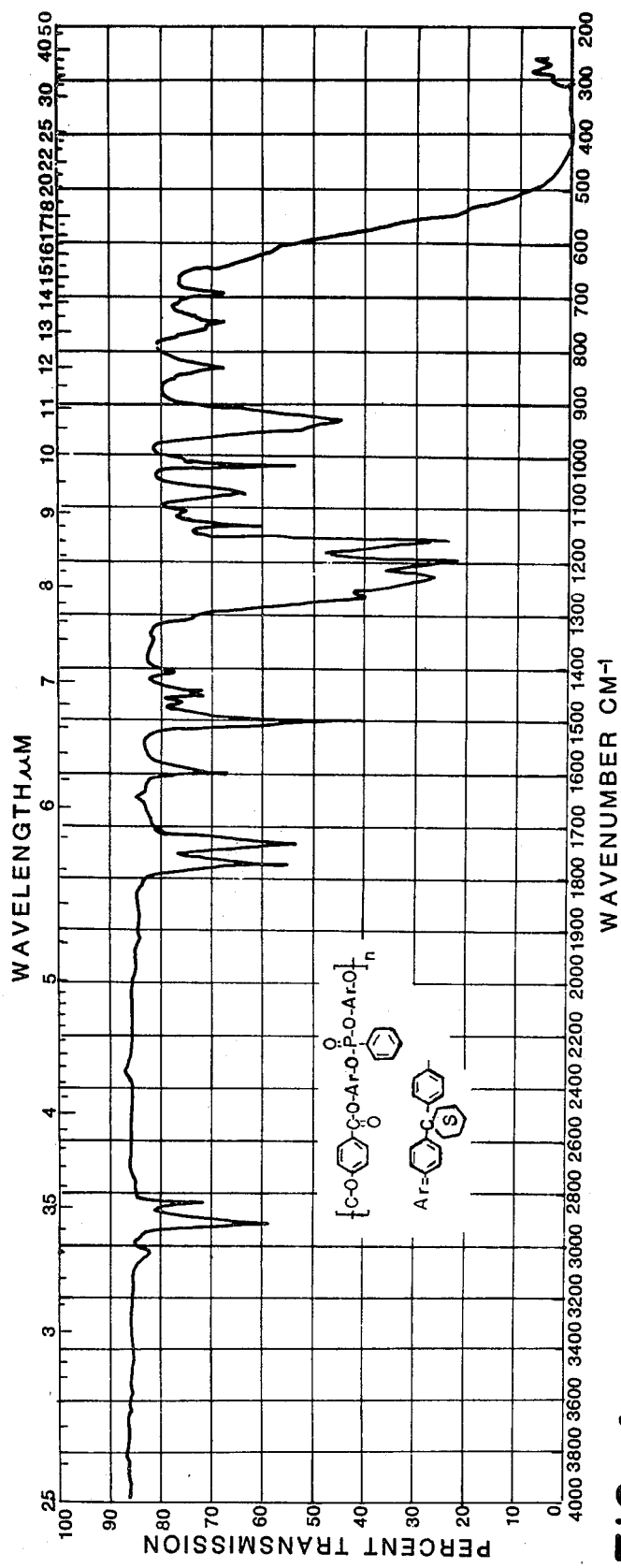
FIG. 4 — IR-spectrum of poly-(1.1-bis (4-oxyphenyl) cyclohexyliden)-phenylphosphonato-1.4 phenylenestercarbonate

THERMOPLASTIC POLYPHOSPHONATOPHENYL ESTER CARBONATE FROM ARYLOXYCARBONYLOXY-BENZOIC ACID ARYL ESTER AND PREPARATION THEREOF

FIELD OF THE INVENTION

The invention is directed to a process for the preparation of thermoplastic polyphosphonatophenyl ester carbonates.

BRIEF DESCRIPTION OF THE INVENTION

A two-step catalyzed process wherein first, a aryloxy carbonyloxy-benzoic acid aryl ester is prepared and (second) then transesterified with a phosphonic acid diphenyl ester and a diphenol to yield a polyphosphonatophenyl ester carbonate corresponding to the structure

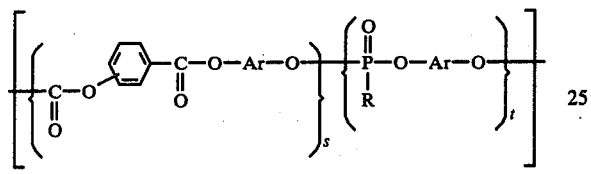

wherein Ar is an aryl radical, R is an aliphatic, cycloaliphatic or an aromatic radical, S is from 1.0 to 19.0 and t is from 19.0 to 1.0 with the proviso that s+t=20.0.

DESCRIPTION OF THE PRIOR ART

Polyphosphonates characterized by their high level of flame retardance and mechanical properties have been taught in U.S. Pat. Nos. 2,682,522; 2,716,101; 2,891,915; 3,719,727; 3,919,363; 3,946,093 and 4,046,724 and in DAS No. 1,569,340 and DOS Nos. 2,458,967 and 2,461,658. Characterized generally by their relatively low molecular weight these prior art resins are unsuitable for thermoplastic processing. Furthermore, these prior art resins are dimensionally unstable at elevated temperatures.

It is also known from German Patent Application No. P 29 25 208.2 that thermoplastic aromatic polyphosphonato carbonates may be prepared by transesterification of diaryl carbonates and phosphonic acid diaryl esters with diphenols in the presence of alkaline transesterification catalysts which may be neutralized at the end of the polycondensation reaction upon the addition of acid. These resins, although of good flame retardance and mechanical properties, exhibit an undesirable level of thermal aging.

Also U.S. Ser. No. 224,077 filed Jan. 12, 1981 teaches polyphosphonato carbonates prepared by transesterification which is catalyzed by neutral catalysts.

The present invention relates to a transesterification process for the preparation of novel polyphospnonatophenyl ester.

DETAILED DESCRIPTION OF THE INVENTION

The invention relates to a process for the preparation of thermoplastic aromatic polyphosphonatophenyl ester carbonates having a weight average molecular weight of at least 11,000, preferably 11,000 to 200,000 and most preferably 20,000 to 80,000 by transesterification in an oxygen-free gas atmosphere under atmospheric pressure or reduced pressure in the presence of a catalyst, the volatile aromatic compounds such as phenol being distilled off.

The process may be described schematically as comprising two steps, namely:

1. a catalyzed reaction between hydroxy benzoic acid

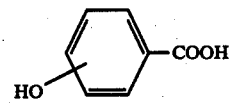

and a molar excess of diaryl carbonate of the general structure

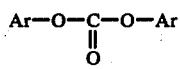

wherein Ar is an aryl radical, to form an aryloxycarbonyloxybenzoic acid aryl ester of the structure

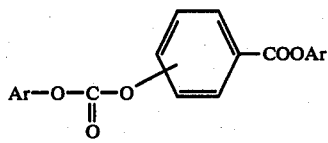

and 2. a transesterification of the product of (1) above with phosphonic acid diaryl ester of the general formula

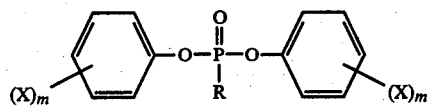

wherein R is an aliphatic or an aromatic radical in the presence of a diphenol and the continued presence of the catalyst referred to at (1) above, with the proviso that the molar amount of the diphenol equals the total molar amount of the aryloxycarbonyloxy-benzoic acid aryl ester and the phosphonic acid diphenyl ester at a temperature of 80° to 400° C. under vacuum, the aromatic volatiles being distilled off to yield the polyphosphonatophenyl ester carbonate of the general formula

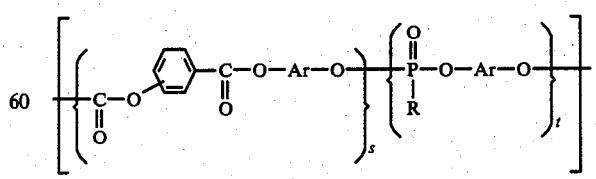

characterized in that s=1.0 to 19.0 and t=19.0 to 1.0 with the proviso that s+t=20.0.

Diaryl carbonates suitable in the practice of the present process may be described as

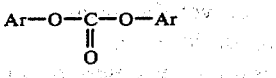

where Ar is an aryl radical preferably having 6 to 14 carbon atoms, in particular, phenyl or $C_1$-$C_4$ alkylsubstituted phenyl. Diphenyl carbonate and di-(p-tolyl) carbonate are particularly suitable whereas, diphenyl carbonate is particularly preferred.

Phosphonic acid diaryl esters suitable according to the present invention may be described as

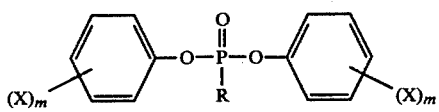

wherein R denotes at least one of $C_1$-$C_{12}$ alkyl, $C_2$-$C_{12}$ alkenyl, $C_6$-$C_{30}$ cycloalkyl, $C_6$-$C_{30}$ cycloalkenyl, $C_6$-$C_{30}$ aryl, $C_7$-$C_{30}$ arylalkyl or $C_8$-$C_{30}$ arylalkenyl, wherein aryl-containing versions, the aryl radical may be unsubstituted or substituted by 1 to 5 $C_1$-$C_4$ alkyl groups, X denotes a $C_1$-$C_4$ alkyl radical or a halogen and n is either 0 or an integer from 1 to 5. Halogen-free phosphonic acid diphenyl esters are preferred and methyl phosphonic acid diphenyl ester and phenylphosphonic acid diphenyl ester are especially preferred.

Among the examples of phosphonic acid diphenyl esters, which are suitable in the process of the invention, are cyclohexylphosphonic acid diphenyl ester, methylphosphonic acid diphenyl ester, ethylphosphonic acid diphenyl ester, 2-phenyl-ethylenephosphonic acid diphenyl ester, butylphosphonic acid diphenyl ester, isopropylphosphonic acid dipenyl ester, and phenylphosphonic acid diphenyl ester.

The diphenols suitable in the practice of the invention may be described by the structural formulas (1) or (2)

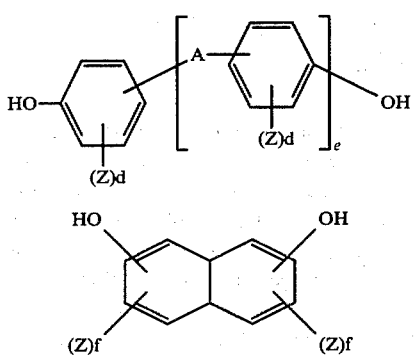

in which
A denotes an alkyelene group with 2 to 4 C atoms, an alkylidene group with 1 to 5 C atoms, a cycloalkylene group with 5 to 6 C atoms, a cycloalkylidene group with 5 to 6 C atoms, a carbonyl group or oxygen,
e denotes the number 0 or 1,
Z denotes F, Cl, Br or $C_1$-$C_4$ alkyl and if several Z radicals are substituents in one aryl radical they may be identical or different,
d denotes 0 or an integer from 1 to 4 and
f denotes 0 or an integer from 1 to 3.

Particularly preferred compounds of the formula (1) are those in which e denotes 1, A denotes the isopropyl-idene radical and d denotes 0, i.e., bisphenol A. In the preferred embodiment the reactants are halogen-free.

The reaction catalysts, present in an amount of from about 0.001 to about 0.05%, relative to the molar amount of the diphenols employed, may be either alkaline or neutral catalysts. Among the alkaline catalysts are alkaline or alkaline earth alcoholates such as sodium ethylate or calcium methylate, alkali phenolates, hydrides of the alkaline or alkaline earth metals, oxides and amides of alkaline or alkaline earth metals and the alkali salts or organic or inorganic acids such as sodium carbonate, sodium acetate and sodium benzoate. These catalysts may be neutralized at the end of the reaction with an equivalent amount of an acidic substance such as dialkylsulfate or an acid chloride such as terephthalic acid dichloride.

Among the neutral catalysts suitable in the context of the reaction are $C_1$-$C_{18}$ tetraalkyl titanates, particularly tetrabutyltitanate, $C_1$-$C_4$ dialkyltin oxides, particularly dibutyltin oxide, $C_1$-$C_4$ dialkyl-$C_1$-$C_4$ dialkyloxytin compounds, particularly dibutyldimethoxytin, $C_3$-$C_{18}$ tetraalkylzirconates, particularly zircon-tetraoctonate, $C_2$-$C_{18}$ trialkylvanadylates, particularly vandylethylate ($=VO(OC_2H_5)_3$) and mixtures of germanium dioxide or titanium dioxide with any of the above-mentioned catalysts. Further, antimony acetate, antimony phosphate, bismuth stannate, bismuth acetate, bismuth benzoate, bismuth titanate, bismuth phenolate, zinc acetate, zinc propionate, tributyltin acetate, tetrabutylstannate, tributyltin benzoate and dibutyltin glycolate are also suitable catalysts. The preferred catalyst is zinc acetate.

The high molecular weight thermoplastic aromatic polyphosponatophenylene ester carbonates obtained by the process according to the invention can be branched by incorporating therewith small amounts, preferably between 0.05 and 3.0 mol % (based on the diphenols employed), of compounds which are trifunctional or more than trifunctional, for example, those with three or more ester or phenolic hydroxyl groups. Triaryl phosphates, such as triphenyl phosphate, can also be cocondensed in the polyphosphonatophenylene ester carbonates as trifunctional branching components in amounts of between 0.05 and 3.0 mol % (based on the total molar amount of the mixture of diaryl carbonate and phosphonic acid diaryl ester employed), whereupon the resulting resin is branched by phosporic acid ester groups.

Examples of some of the branching phenolic compounds with three or more than three phenolic hydroxyl groups which can be used are phloroglucinol, 4,6-dimethyl-2,4,6-tri-(4-hydroxyphenyl)-hept-2-ene, 4,6-dimethyl-2,4,6-tri-(4-hydroxyphenyl)-heptane, 1,3,5-tri-(4-hydroxyphenyl)-benzene,1,1,1-tri-(4-hydroxyphenyl)-ethane, tri-(4-hydroxyphenyl)-phenylmethane,2,2-bis-[4,4-bis-(4-hydroxyphenyl)-cyclohexyl]-propane, 2,4-bis-(4-hydroxyphenyl-isopropyl)-phenol, 2,6-bis-(2-hydroxy-5'-methylbenzyl)-4-methylphenol, 2-(4-hydroxyphenyl)-2-(2,4-dihydroxyphenyl)-propane and 1,4-bis-(4,4''-dihydroxytriphenylmethyl)-benzene.

Other branching agents suitable in the present context are those mentioned in DOS Nos. 1,570,533, 2,116,974, and 2,113,347, British Pat. Nos. 885,442 and 1,079,821 and U.S. Pat. Nos. 3,544,514 and 4,185,009, all incorporated herein by reference.

All the starting materials employed for the transesterification should have a purity of >99.1% by weight, preferably >99.6% by weight.

The preferred branching agents are trimesintriphenylate of the structure

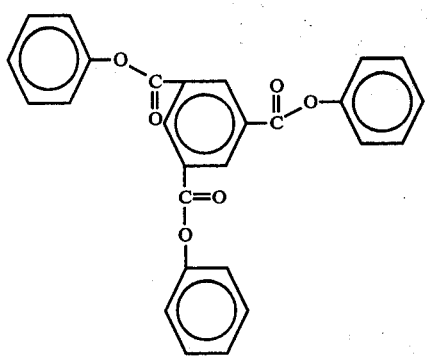

or triphenylisocyanurate of the structure

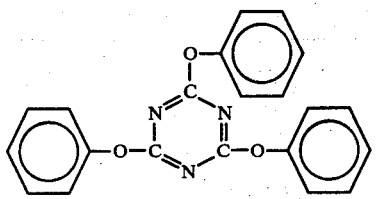

EXAMPLES

EXAMPLE 1

In a reaction vessel were introduced 27.6 gm (0.2 mol) of a p-hydroxybenzoic acid and reacted with 94.2 gm (0.44 mol) of diphenyl carbonate in the presence of about 10 mg of zinc acetate as catalyst at about 250° C. About 37.6 gm of phenol and about 8.6 gm of diphenyl carbonate were distilled off. To the reaction vessel were then added 91.2 gm (0.4 mol) of bisphenol A and 49.6 gm (0.2 mol) of diphenyl methylphosphonate ester and the temperature increased to about 305° C. over three hours and held at that temperature for an additional period of 75 minutes. During the heat-up period, the vacuum was gradually reduced from about 150 to 5 mm Hg and further reduced to about 0.9 mm during the period of constant temperature. During the reaction about 132 ml of volatile aromatics were distilled off.

EXAMPLE 2

In a procedure similar to that described in Example 1, 27.6 gm (0.2 mol) of p-hydroxy benzoic acid and 94.2 gm (0.44 mol) of diphenyl carbonate were reacted in the presence of 10 mg of zinc acetate under nitrogen. After one hour and 50 minutes, during which period the temperature was increased to 275° C. and the vacuum gradually to 150 mm Hg, and about 37 ml of phenol distilled off, 91.2 gm (0.4 mol) of bisphenol A and 62.0 gm (0.2 mol) of diphenyl phenylphosphonate were added. Increased temperature to 295 and vacuum to 5 mm Hg over a period of 85 minutes was accompanied by distilling off of phenol (81 ml). The temperature was kept constant at 298° C. for the next 75 minutes during which time the vacuum was gradually reduced to about 0.9 mm Hg and further 2 ml of phenol driven off.

Upon ending the polycondensation reaction, the melt is converted in a known manner into granules for further molding or directly into end products such as films or fibers.

The resins prepared in accordance with Examples 1 and 2 above, conforming to the structural formula

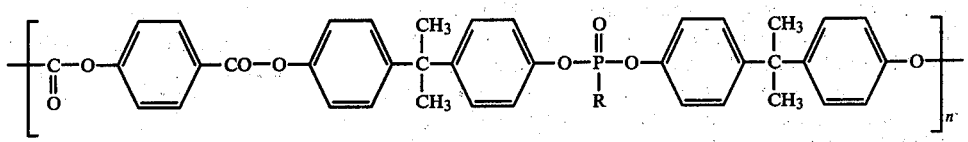

where R is $CH_3$ (Example 1) or $C_6H_5$ (Example 2) were analyzed as follows:

TABLE 1

| EXAMPLE | 1 | 2 |
|---|---|---|
| glass transition temperature[1], °C. | 127.1 | 127.8 |
| molecular weight, weight average | 11,600 | 17,300 |
| number average | 42,600 | 53,600 |
| relative viscosity[2] | 1.517 | 1.377 |
| % phosphorous | 4.71 | 4.38 |
| Index of Refraction | 1.594 | 1.604 |
| Abbe number | 28.4 | 28.2 |

[1] measured by differential scanning colorimetry
[2] measured in a 0.5% solution in methylenedichloride at 25° C.

Films cast from a methylene chloride solution of the resins of Examples 1 and 2 were further analyzed as to their IR spectra shown here as FIGS. 1 and 2 respectively.

EXAMPLES 3-5

The Table below reports the glass transition temperature measured on some resins prepared according to the process disclosked above. Glass transition temperature values were determined by differential scanning calorimetry at a heating rate of 20° C./min. and under a 20 cc/min. $N_2$ purge.

TABLE 2

| EXAMPLE NUMBER | STRUCTURE | TG° |
|---|---|---|
| 3 | (structure shown) R = —CH₃ | 139.0 |
| 4 | Same as above but with R = —C₆H₅ (phenyl) | 137.5 |
| 5 | (structure shown with subscripts 0.8 and 1.2/n) | 118.7 |

The synthesis route of Examples 3–5 were carried out in much the same way as described above in Examples 1 to 2. Specifically however, the poly-[1.1-bis-(4-oxyphenyl) cyclohexyliden]-methylphosphonato-1.4-phenylene estercarbonate of Example 3 enatiled 27.6 gm (0.2 mol) of p-hydroxybenzoic acid and 94.1 gm (0.44 mol) of diphenyl-carbonate reacting, in the presence of about 10 mg of zinc acetate at about 270° C. About 37.6 gm of phenol and 8.5 gm of diphenyl carbonate were distilled off. To the reaction vessel were then added 107.2 gm (0.4 mol) of 1.1-bis(4-hydroxyphenyl)-cyclohexane and 49.6 gm (0.2 mol) of diphenyl methylphosphonate. The temperature of the reaction was increased to 295° C. and the vacuum reduced to 0.5 torr. The relative viscosity of the resulting reaction product was measured on a 0.5 wt. percent solution in methylene chloride, to be 1.289. The elemental analysis indicated the resin to consist of

C: 72.79%
H: 5.72
P: 4.20
O: 17.12

In Example 4 the preparation of poly-[1.1-bis-(4-oxyphenyl) cyclohexyliden]-phenylphosphonato-1,4-phenylene-ester carbonate, entailed 27.6 gm (0.2 mol) of p-hydroxybenzoic acid, 94.1 gm (0.44 mol) diphenyl carbonate and 10 mg of zinc acetate as catalyst, at a reaction temperature of 270° C. After distillation of phenol and diphenyl carbonate, 107.2 gm (0.4 mol) of 1.1-bis(4-hydroxyphenyl)-cyclohexane and 62.0 gm (0.2 mol) of diphenyl-phenyl phosphonate were added and the reaction temperature increased to 295° C. and the vacuum reduced to 0.5 torr. The relative viscosity, determined as described above, was 1.243, and the elemental analysis of the resin showed.

C: 74.51%
H: 5.54
P: 3.90
O: 15.90

The corresponding reactants entailed in Example 5 were 22.1 gm (0.16 mol) of p-hydroxybenzoic acid, 75.28 gm (0.352 mol) of diphenyl carbonate, 10 mg zinc acetate as catalyst, 91.2 gm (0.4 mol) of bisphenol A, and 74.4 gm (0.24 mol) of diphenyl phenylphosphonate.

The relative viscosity, measured as above, was 1.230 and the elemental analysis showed

C: 72.68%
H: 5.18
O: 16.95
P: 5.20

Cast films on the polymers of the invention were prepared from a methylene chloride solution.

The IR spectra of the resins prepared in Examples 3 to 4 are shown as FIGS. 3 and 4 respectively.

The polyphosphonatophenyl ester carbonates of the present invention are soluble in halogenated hydrocarbons, THF, dioxane, phenol, cresol, DMF and DMSO.

The resins of the present invention may be admixed with at least one of pigments, antistatic agents, mold release agents, heat stabilizers, UV stabilizers and reinforcing agents or fillers to obtain special properties.

The resins may be molded by injection or extruded at about 240° C. to 320° C.

The characteristic spectra shown in the figures may be summarized as in Table below.

| | Maxima (wave number in cm⁻¹) |
|---|---|
| FIG. 1 | 2970, 1775, 1740, 1605, 1505, 1318, 1230, 1200, 1160, 1018, 932 |
| FIG. 2 | 2960, 1772, 1737, 1600, 1500, 1225, 1195, 1160, 1130, 1065, 1010, 925, 835 |
| FIG. 3 | 2935, 2860, 1773, 1740, 1600, 1503, 1315, 1265, 1228, 1200, 1160, 1012, 930, 828 |
| FIG. 4 | 2938, 2860, 1775, 1740, 1600, 1502, 1265, 1228, 1195, 1160, 1130, 1070, 1012, 928 |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of thermoplastic aromatic polyphosphonatophenyl ester carbonates comprising
   (i) reacting a hydroxy benzoic acid with a molar excess of diaryl carbonate of the structure

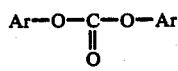

wherein Ar is an aryl radical, in the presence of an alkaline or neutral transesterification catalyst, to obtain a aryloxycarbonyloxybenzoic acid aryl ester of the structure

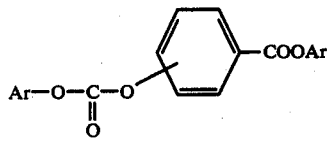 (1)

wherein Ar is as defined above, and
(ii) transesterifying said (1) with phosphonic acid diaryl ester of the structure

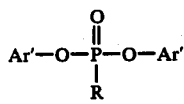 (2)

wherein Ar' is a substituted or an unsubstituted aromatic radical and R is selected from the group consisting of at least one of $C_1$-$C_{12}$ alkyl, $C_2$-$C_{12}$ alkenyl, $C_6$-$C_{30}$ cycloalkenyl, $C_6$-$C_{30}$ aryl, $C_7$-$C_{30}$ arylalkyl or $C_8$-$C_{30}$ arylalkenyl and (3) a diphenol reactant in continuous contact with said catalyst, at a temperature of about 80° to 400° C. under vacuum, with the proviso that the molar amount of said diphenol equals the total molar amount of said (1) and said (2).

2. The process of claim 1 wherein said hydroxy benzoic acid is 4-hydroxy benzoic acid.

3. The process of claim 1 wherein said R is —$CH_3$.

4. The process of claim 1 wherein said R is a phenyl radical.

5. The process of claim 1 wherein said diphenol is bisphenol A.

6. The polyphosphonatophenyl ester carbonate prepared in accordance with the process of claim 1.

7. A thermoplastic polymeric compound characterized by the molecular structure

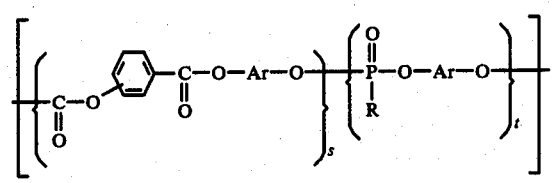

wherein Ar is an arylene radical, R is selected from the group consisting of aliphatic, cycloaliphatic and aromatic radicals, s is from 1.0 to 19.0 and t is from 19.0 to 1.0 and the sum of s and t equals 20.0.

* * * * *

UNITED STATES PATENT AND TRADEMARK OFFICE
CERTIFICATE OF CORRECTION

PATENT NO. : 4,381,390
DATED : April 26, 1983
INVENTOR(S) : Manfred Schmidt and Ludwig Bottenbruch It is certified that error appears in the above—identified patent and that said Letters Patent is hereby corrected as shown below:

At Figure 1, please delete the formula and insert therefor

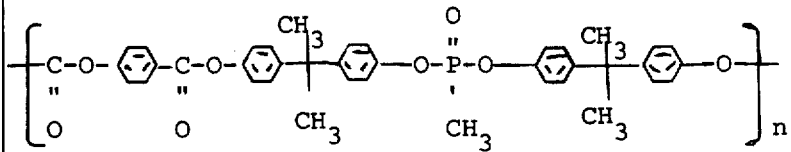

At Figure 3, please delete the formula and insert therefor

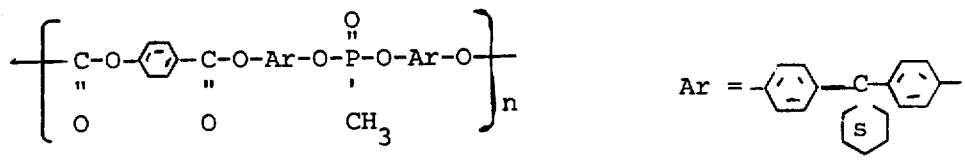

At column 3, at about line 50, please delete the formula and insert therefor

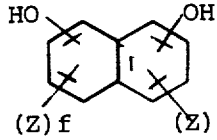

At column 3, line 56, please delete "alkyelene" and insert therefor --alkylene--.

At column 5 at about lines 23-28 kindly delete the formula.

At column 6, line 13, after "gradually" and before the word "to", please insert the word --reduced--; and in the same line please delete the word "and".

UNITED STATES PATENT AND TRADEMARK OFFICE
CERTIFICATE OF CORRECTION

PATENT NO. : 4,381,390

DATED : April 26, 1983

INVENTOR(S) : Manfred Schmidt and Ludwig Bottenbruch

It is certified that error appears in the above—identified patent and that said Letters Patent is hereby corrected as shown below:

At column 6, line 16, after "295", kindly insert --°C--.

At column 6, line 65, kindly delete "disclosked" and insert --disclosed--therefor.

At column 7, line 30, kindly delete "enatiled" and insert --entailed-- therefor.

Signed and Sealed this

Thirteenth Day of September 1983

[SEAL]

Attest:

GERALD J. MOSSINGHOFF

Attesting Officer

Commissioner of Patents and Trademarks